US012577275B2

(12) United States Patent
Sota et al.

(10) Patent No.: US 12,577,275 B2
(45) Date of Patent: Mar. 17, 2026

(54) HYDROPHOBIC INTERACTION CHROMATOGRAPHY CARRIER AND PROTEIN PURIFICATION METHOD

(71) Applicant: JNC CORPORATION, Tokyo (JP)

(72) Inventors: Kojiro Sota, Yokohama (JP); Yoshihiro Matsumoto, Yokohama (JP)

(73) Assignee: JNC CORPORATION, Tokyo (JP)

(*) Notice: Subject to any disclaimer, the term of this patent is extended or adjusted under 35 U.S.C. 154(b) by 747 days.

(21) Appl. No.: 17/407,106

(22) Filed: Aug. 19, 2021

(65) Prior Publication Data

US 2022/0064211 A1 Mar. 3, 2022

(30) Foreign Application Priority Data

Sep. 3, 2020 (JP) ................................ 2020-148381

(51) Int. Cl.

*C07K 1/20* (2006.01)
*B01J 20/24* (2006.01)
*B01J 20/286* (2006.01)

(52) U.S. Cl.

CPC ................ *C07K 1/20* (2013.01); *B01J 20/24* (2013.01); *B01J 20/286* (2013.01)

(58) Field of Classification Search

CPC .. C07K 1/20; C07K 16/00; B01J 20/24; B01J 20/286; B01J 20/28004; B01J 20/289; B01J 20/321; B01J 20/3212; B01J 20/3219; B01J 20/3253; B01D 15/327
See application file for complete search history.

(56) References Cited

FOREIGN PATENT DOCUMENTS

| | | | | |
|---|---|---|---|---|
| EP | 2266675 A2 * | 12/2010 | ........... | B01D 15/265 |
| WO | 2014145208 | 9/2014 | | |

OTHER PUBLICATIONS

Cytiva et al. (Phenyl Sepharose 6 Fast Flow, Instructions for Use, Jul. 2020, 30 pages) (Year: 2020).*
Yoo et al. (J Membrane Sci, 2012, 390:263-269) (Year: 2012).*
Abhinav A. Shukla et al., "Recent advances in large-scale production of monoclonal antibodies and related proteins," Trends in Biotechnology, vol. 28, Mar. 2010, pp. 253-261.
Abhinav A. Shukla et al., "Downstream processing of monoclonal antibodies—Application of platform approaches," Journal of Chromatography B, vol. 848, Mar. 2007, pp. 28-39.

* cited by examiner

*Primary Examiner* — David Steadman
*Assistant Examiner* — Joseph R Spangler
(74) *Attorney, Agent, or Firm* — JCIPRNET

(57) ABSTRACT

A chromatography carrier capable of removing an antibody dimer from a solution containing an antibody monomer. The chromatography carrier includes a base carrier containing porous particles and a hydrophobic ligand bound to the base carrier, and has an electric conductivity of 34 mS/cm or less measured by a gradient elution test. The porous particles preferably have an average particle diameter of 66 to 150 μm, and the hydrophobic ligand preferably has at least one selected from a group consisting of phenyl, n-butyl, n-hexyl, n-octyl, and n-octadecyl.

6 Claims, 3 Drawing Sheets

(Example 3)

(Example 4)

HYDROPHOBIC INTERACTION CHROMATOGRAPHY CARRIER AND PROTEIN PURIFICATION METHOD

CROSS-REFERENCE TO RELATED APPLICATION

This application claims the priority benefit of Japan application serial no. 2020-148381, filed on Sep. 3, 2020. The entirety of the above-mentioned patent application is hereby incorporated by reference herein and made a part of this specification.

BACKGROUND

Technical Field

The disclosure relates to a hydrophobic interaction chromatography carrier and a protein purification method using the same.

Related Art

Purification of biopharmaceuticals using chromatography is widely known, in which various intermolecular interactions are used to separate a subject matter and a foreign matter. Examples include ion exchange chromatography utilizing an electrostatic interaction, hydrophobic interaction chromatography utilizing a hydrophobic interaction, protein A chromatography utilizing an affinity interaction with respect to an antibody, and the like.

In the above examples, the hydrophobic interaction chromatography (HIC) is used for a purpose of reducing a step-related foreign matter such as an antibody aggregate, a host cell-derived protein, a leaked protein A, or the like in a final purification step of a purification process of a monoclonal antibody (Non-Patent literatures 1 and 2).

When the HIC is used, a kosmotropic salt with high concentration is usually used to promote a hydrophobic interaction between a HIC carrier and the subject matter or foreign matter. On the other hand, a HIC method has also been developed which can remove the aggregate in a flow-through mode under an unsalted condition (Patent literature 1).

However, there is no chromatography carrier which can recover the protein, especially the antibody, but is also excellent in removing a dimeric antibody in the aggregate of the antibody.

LITERATURE OF RELATED ART

Patent Literature

[Patent literature 1] International Publication No. 2014/145208

Non-Patent Literature

[Non-Patent literature 1] Shukla and Thommes, Trends in Biotechnol 28 (5): 253-261, 2010

[Non-Patent literature 2] Shukla et al., J. Chromatogr. B 848:28-39, 2007

SUMMARY

Problems to be Solved

The disclosure provides a HIC carrier excellent in removing a dimer of an antibody, and a method for recovering an antibody solution from which the dimer has been removed using the carrier.

Means to Solve Problems

As a result of diligent studies to solve the above problems, the inventors have found that a chromatography carrier obtained by adding a hydrophobic group to a base carrier containing porous particles has an excellent property of removing a dimer, and completed the disclosure. That is, the disclosure is, for example, as follows.

[1] A chromatography carrier, including a base carrier containing porous particles and a hydrophobic ligand bound to the base carrier, and having an electric conductivity of 34 mS/cm or less measured by a gradient elution test.

[2] The chromatography carrier according to [1], wherein the porous particles have an average particle diameter of 66 to 150 μm.

[3] The chromatography carrier according to [1] or [2], wherein the hydrophobic ligand has at least one selected from a group consisting of phenyl, n-butyl, n-hexyl, n-octyl, and n-octadecyl.

[4] The chromatography carrier according to any one of [1] to [3], wherein the porous particles include crosslinked cellulose.

[5] A method for purifying an antibody, including a step of bringing the chromatography carrier according to any one of [1] to [4] into contact with an antibody solution and a step of recovering the solution, thereby obtaining a solution from which a dimer has been removed.

[6] The method for purifying an antibody according to [5], wherein the step of contacting with the antibody solution includes a step of passing the antibody solution through a container containing the chromatography carrier in a flow-through mode.

[7] The method for purifying an antibody according to [5] or [6], wherein the antibody is a monoclonal antibody or a polyclonal antibody.

[8] The method for purifying an antibody according to [7], wherein the antibody is a human antibody, a mouse antibody, or a chimeric antibody.

Effect

According to the disclosure, a chromatography carrier excellent in removing a dimeric antibody can be provided.

DESCRIPTION OF THE EMBODIMENTS

Figure 1:
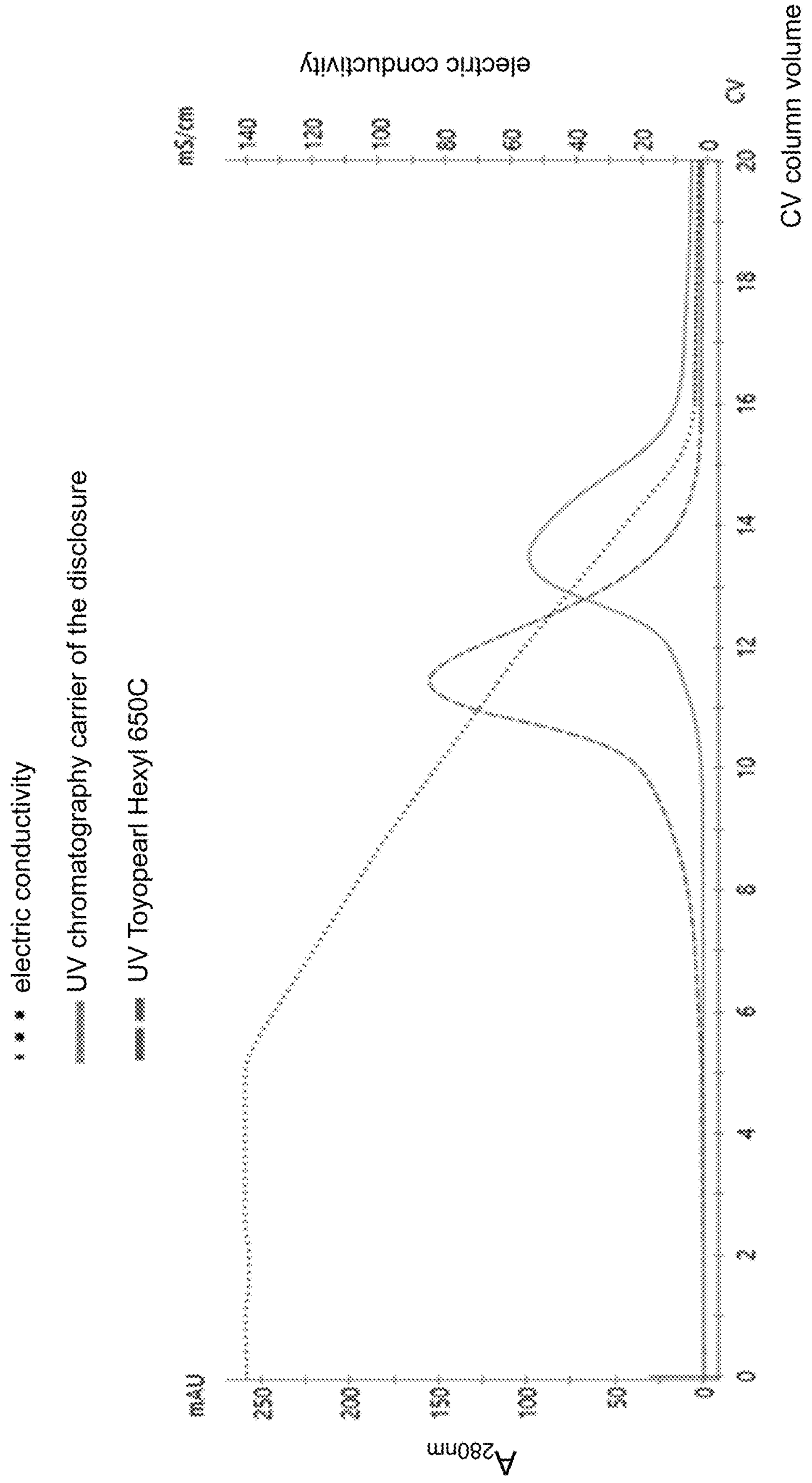
FIG. 1 shows linear retention data of each chromatography carrier tested in Example 1.

Specified terms are defined first in order that the disclosure can be more easily understood. Further definitions are described throughout the detailed description.

A term “preparative chromatography device” has two types of pumps and can send at least two types of solutions respectively. In addition, there are at least two types of detectors including a UV detector and an electric conductivity meter which are connected in the order of the UV detector and the electric conductivity meter.

A term “gradient elution test” refers to a test in which a 20 mM of sodium phosphate buffer solution containing 1 M of ammonium sulfate at pH 7.0 is flowed through a chromatography carrier packed in a column having a column capacity of 1.06 mL using a preparative chromatography device at a flow rate of 0.25 column volume/min for 5 column volumes; then a 1 mg/mL lysozyme solution dissolved in the 20 mM of sodium phosphate buffer solution containing 1 M of ammonium sulfate at pH 7.0 is flowed at a flow rate of 0.25 column volume/min for 1 column volume; thereafter the 20 mM of sodium phosphate buffer solution containing 1 M of ammonium sulfate at pH 7.0 is flowed at a flow rate of 0.25 column volume/min for 2 column volumes; thereafter the 20 mM of sodium phosphate buffer solution at pH 7.0 is flowed at a flow rate of 0.25 column volume/min for 10 column volumes; and then a solution at the time of the appearance of an elution peak top of lysozyme measured at a transmitted light of 280 nm by an absorbance meter having a flow cell with a capacity of 2 μL or less is measured by an electric conductivity meter having a flow cell with a capacity of 50 μL or less and connected to the absorbance meter via a tube having a capacity of 20 μL or less. By the test, an electric conductivity of the buffer solution is observed in which the lysozyme is eluted from the chromatography carrier, or it is observed that the lysozyme is not eluted.

The term “20 mM of sodium phosphate buffer solution containing 1 M of ammonium sulfate at pH 7.0” refers to an aqueous solution obtained in a manner that 132.14 g of ammonium sulfate and 2.40 g of sodium dihydrogen phosphate are dissolved in per 1 L of solution and the obtained solution is adjusted to pH 7.0 by sodium hydroxide.

The term “20 mM of sodium phosphate buffer solution at pH 7.0” refers to an aqueous solution obtained in a manner that 2.40 g of sodium dihydrogen phosphate is dissolved in per 1 L of solution and adjusted to pH 7.0 by sodium hydroxide.

A term “Tris” refers to trishydroxymethyl aminomethane.

A term “buffer solution at pH 6.0 containing 20 mM of Tris acetate+50 mM of NaCl” refers to an aqueous solution containing 1.20 g of acetic acid and 2.92 g of sodium chloride in per 1 L of solution and adjusted to pH 6.0 by Tris.

A term “buffer solution at pH 6.7 containing 200 mM of sodium phosphate+100 mM of sodium sulfate” refers to an aqueous solution obtained in a manner that 24.0 g of sodium dihydrogen phosphate and 14.2 g of sodium sulfate are dissolved in per 1 L of solution and adjusted to pH 6.7 by sodium hydroxide.

A term “solution at pH 7.0 containing 20 mM of Tris acetate+10 mS/cm NaCl” refers to a solution obtained in a manner that 5 M of NaCl solution is added to an aqueous solution containing 1.20 g of acetic acid in per 1 L of solution and adjusted to pH 7.0 by Tris until an electric conductivity reaches 10 mS/cm.

A term “antibody” refers to an immunoglobulin molecule capable of specifically binding to a target, such as carbohydrate, polynucleotide, lipid, polypeptide, or the like by at least one antigen discriminator located in a variable region of the immunoglobulin molecule. As used in the present specification, the antibody is not only a raw (for example, full-length) polyclonal antibody or a raw monoclonal antibody, but also includes an antigen-binding fragment of the antibody (Fab, Fab', F(ab')2, Fv, and the like), a single chain (scFv), a mutant of the antibody, a fusion protein containing an antibody potion, a humanized antibody, a chimeric antibody, a bispecific antibody, a linear antibody, a single chain antibody, a multi-specific antibody (for example, a bispecific antibody), and other modified arrangements of the immunoglobulin molecule containing a required specific antigen discriminator and containing a glycosylation mutant of the antibody, an amino acid sequence mutant of the antibody, and a covalent modification antibody. The antibody includes an antibody of any class such as IgD, IgE, IgG, IgA, IgM (or a subclass thereof), or the like, but the antibody does not need to be of any specified class. An immunoglobulin may be assigned to different classes according to an antibody amino acid sequence of an invariant region of a heavy chain. There are five major classes of immunoglobulins including IgA, IgD, IgE, IgG, and IgM, and several of these immunoglobulins may be further divided into subclasses (isotypes), for example. IgG1, IgG2, IgG3, IgG4, IgA1, and IgA2.

A term “dimer” refers to an antibody in which two molecules are bound.

A term “aggregate” refers to an antibody in which three or more molecules are bound.

A term “remove” refers to removing non-monomers from an antibody solution containing a monomer. For example, a state in which the dimer has been removed refers to a state in which when an antibody solution containing the dimer is brought into contact with the chromatography carrier, the chromatography carrier retains the dimer, and thereby a mass of the dimer in a recovered solution is less than a mass of the dimer in a loaded solution.

The term “load” refers to an operation in which a solution containing an antibody is passed through the chromatography carrier packed in the column via one mouth of the column to bring the chromatography carrier into contact with the solution containing the antibody, and the solution containing the antibody is taken out via the other mouth.

A term “flow-through mode” refers to a separation technique for preparation of a product, herein it is intended that at least one product included in preparation products flows through the chromatography carrier, and on the other hand, at least one potential contaminant or foreign matter binds to chromatography resin or medium.

Hereinafter, constituent elements of the chromatography carrier of the disclosure are described in order.

1. Base Carrier

The chromatography carrier generally has a configuration in which a ligand is bound to a base carrier. The base carrier in the disclosure contains porous particles, and the porous particles are modified with a functional group (for example, a hydroxyl group, a carbamoyl group, or the like) for introducing a hydrophobic ligand serving as the ligand. The used porous particles are not limited as long as the porous particles can be modified by this functional group, and preferably may be, for example, a polysaccharide such as agarose, dextran, starch, cellulose, pullulan, chitin, chitosan, cellulose triacetate, cellulose diacetate, or the like, and a derivative of the polysaccharide; an organic polymer such as polyacrylamide, polymethacrylamide, polyacrylate, polymethacrylate, polyalkyl vinyl ether, polyvinyl alcohol, or the like; and the like. The porous particles are preferable to form a crosslinked structure from the viewpoint of being capable of ensuring a mechanical strength. Among these porous particles, a crosslinked cellulose particle is more preferably used in which a skeleton of the cellulose particle is reinforced by a crosslinking reaction.

The crosslinked cellulose particle is not particularly limited as long as the crosslinked cellulose particle can be used as the base carrier of the chromatography carrier. The cellulose used as a raw material may be crystalline cellulose or non-crystalline cellulose, but the crystalline cellulose is preferable because of a high strength.

The crosslinked cellulose particle that can be preferably used in the disclosure may be, for example, a porous cellulose gel disclosed in Japanese Patent Laid-Open No. 2009-242770. The porous cellulose gel disclosed in the same publication can be obtained by a method including a step in which in the presence of at least one inorganic salt selected from a group consisting of a hydrochloride, a sulfate, a phosphate, and a borate in an amount of 6 to 20 times the number of moles of a cellulose monomer, a crosslinking agent in an amount of 4 to 12 times the number of moles of the cellulose monomer and an alkali in an amount of 0.1 to 1.5 times the number of moles of the crosslinking agent are continuously added dropwise or dividedly added for 3 hours to a suspension of an un-crosslinked cellulose particle. The crosslinked cellulose particle obtained in this way has a high mechanical strength and can be used under chromatographic conditions such as a fast flow rate, and a HIC carrier having a high productive can be provided. Here, the "cellulose monomer" refers to a glucose unit which is a constituent unit of the cellulose. In addition, the number of moles of the cellulose monomer (that is, a degree of polymerization) is calculated based on the amount of moisture subtracted from one unit of glucose (that is, a dry weight of the cellulose) (162 molecular weight is set to one mole).

A shape of the porous particles is not particularly limited, but a spherical porous particle is preferable because the spherical porous particle has a high mechanical strength and an excellent gel sedimentation property, and can produce a uniform packed bed. In this case, a sphericity of the porous particle is preferably 0.8 to 1.0. Here, the "sphericity" refers to a minor diameter/major diameter of the porous particle.

A spherical cellulose particle can be easily obtained by, for example, dissolving and regenerating the crystalline cellulose or a cellulose including a crystalline region and a non-crystalline region. A method for manufacturing the spherical cellulose particle may be, for example, a method via acetate esters described in Japanese Patent Publication No. 55-39565. Japanese Patent Publication No. 55-40618, and the like; a method for manufacturing from a solution containing a calcium thiocyanate salt described in Japanese Patent Publication No. 63-62252 and the like; a method for manufacturing from a solution containing paraformaldehyde and dimethyl sulfoxide described in Japanese Patent Laid-Open No. 59-38203 and the like; a method for manufacturing from a cellulose solution obtained in a manner that the cellulose is dissolved in a lithium chloride-containing amide described in Japanese Patent No. 3663666; and the like. In addition, a spherical crosslinked cellulose particle can be obtained by crosslinking the spherical cellulose particle.

A particle diameter of the porous particles used in the disclosure is preferably 10 to 500 μm, and particularly preferably 50 to 150 μm. In addition, an average particle diameter is preferably 66 to 150 μm. Here, the "particle diameter" refers to an actually-measured value of the particle diameter of each porous particles, and the "average particle diameter" refers to an average value calculated based on the above particle diameter.

In the present specification, the particle diameter and the average particle diameter of the porous particles can be measured using, for example, a laser diffraction/scattering type particle diameter distribution measuring device. In the device, a particle group is irradiated with a laser light, a particle size distribution is obtained from an intensity distribution pattern of a diffracted/scattered light emitted from the particle group, and the particle diameter and the average particle diameter are calculated based on the particle size distribution. As a specific measuring device, a particle diameter distribution measuring device LA-950 of a laser diffraction/scattering type (manufactured by HORIBA. Ltd.) or the like can be used.

Alternatively, the particle diameter can also be measured using an image taken by an optical microscope. Specifically, a vernier caliper or the like is used to measure a particle diameter on the image, and an original particle diameter is obtained from a photographing magnification. Besides, the average particle diameter is calculated from values of each particle diameter obtained from the optical microscope image by the following formula.

$$\text{Volume average particle diameter (MV)}=\Sigma(nd^4)/\Sigma(nd^3)$$

[In the formula, d represents the value of the particle diameter of each particle obtained from the optical microscope image, and n represents the number of measured particles.]

Porosity of the porous particles can be characterized by having a pore size property. A gel partition coefficient Kav is one of indexes showing the pore size property. A pore size affects a physical strength of the particle and a diffusivity in the porous particles of a target substance to be purified. Thus, the pore size causes a difference between a flow rate of a liquid passing through the porous particles and a dynamic adsorption capacitance of the porous particles. Therefore, a design of porous particles having a pore size corresponding to the purpose is necessary. Particularly, from the viewpoint of the dynamic adsorption capacitance, when standard polyethylene oxide having a weight average molecular weight of $1.5\times10^5$ Da is used as a sample and pure water is used as a mobile phase, the gel partition coefficient Kav of the porous particles is preferably in a range of 0.15 to 0.6, more preferably in a range of 0.2 to 0.55, and particularly preferably in a range of 0.3 to 0.5.

In the disclosure, porous particles having a pore size capable of obtaining a gel partition coefficient in the above range are preferably used from the viewpoint of an adsorption property. When the crosslinked cellulose particles are used as the porous particles, the gel partition coefficient Kav thereof can be adjusted by, for example, controlling a dissolution concentration of the cellulose during particle formation.

The gel partition coefficient Kav can be obtained by the following formula from a relationship between a retention capacitance and a column volume when a standard substance having a specified molecular weight (for example, polyethylene oxide) is used as a sample.

$$Kav=(Ve-V0)/(Vt-V0)$$

[In the formula. Ve represents a retention capacitance (mL) of the sample, Vt represents an empty column volume (mL), and V0 represents a retention capacitance (mL) of blue dextran.]

A specific method for measuring the gel partition coefficient Kav is described in, for example, L. Fischer's Biochemical Experimental Method 2: "Gel Chromatography". 1st Edition (Tokyo Kagaku Dojin), and the like.

2. Ligand

The chromatography carrier of the disclosure contains the hydrophobic ligand as the ligand. The hydrophobic ligand used in the disclosure is not particularly limited as long as the hydrophobic ligand can bind to the functional group on the base carrier. Specifically, phenyl, n-butyl, n-hexyl, n-octyl, n-octadecyl, and the like can be mentioned, and especially the phenyl is preferable. As a preferable structure of the hydrophobic ligand, a structure of the following formula (1) can be mentioned.

(1)

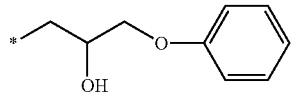

[Reference numeral * denotes a binding site of the ligand to base particles.]

A method for adding the hydrophobic ligand to the base carrier is not particularly limited, and a known method can be used to perform the adding. For example, the hydrophobic ligand can be added to the base carrier in a manner that the hydrophobic ligand is modified with a functional group to which the hydrophobic ligand can be bound (for example, an epoxy group, or the like), and a solution containing the porous particles and a hydrophobic ligand raw material is stirred under predetermined conditions. A preferable hydrophobic ligand raw material may be a structure of the following formula (2).

(2)

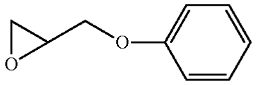

Hereinafter, the gradient elution test of the chromatography carrier and a method for purifying a protein of the disclosure are described.

In an exemplary embodiment of the disclosure, the chromatography carrier is packed in the column. As a specific column, Super Edge Empty Mini Columns Kit (manufactured by JNC Corporation) can be used, but the column is not limited hereto.

The disclosure is based on a surprising recognition of data showing dimer removability superior to an existing HIC carrier by using a chromatography carrier of which an electric conductivity is 34 mS/cm or less. The electric conductivity is at the time when the 20 mM of sodium phosphate buffer solution containing 1 M of ammonium sulfate at pH 7.0 is flowed through the chromatography carrier packed in the column having a column capacity of 1.06 mL using the preparative chromatography device at a flow rate of 0.25 column volume/min for 5 column volumes; then a 1 mg/mL lysozyme solution dissolved in the 20 mM of sodium phosphate buffer solution containing 1 M of ammonium sulfate at pH 7.0 is flowed at a flow rate of 0.25 column volume/min for 1 column volume; thereafter the 20 mM of sodium phosphate buffer solution containing 1 M of ammonium sulfate at pH 7.0 is flowed at a flow rate of 0.25 column volume/min for 2 column volumes; thereafter the 20 mM of sodium phosphate buffer solution at pH 7.0 is flowed at a flow rate of 0.25 column volume/min for 10 column volumes; and then a solution at the time of the appearance of an elution peak top of lysozyme measured at a transmitted light of 280 nm by the absorbance meter having a flow cell with a capacity of 2 μL or less is measured by the electric conductivity meter having a flow cell with a capacity of 50 μL or less and connected to the absorbance meter via the tube having a capacity of 20 μL or less.

In the exemplary embodiment of the disclosure, as the antibody solution, the one obtained by clarifying a CHO cell supernatant and being purified by a protein A carrier may be used.

The method provided in the present specification is particularly useful for purifying the antibody. In the exemplary embodiment of the disclosure, the antibody disclosed herein is an IgG1 antibody. Heavy chain invariant regions corresponding to different classes of immunoglobulins are respectively referred to alpha, delta, epsilon, gamma, and mu. A subunit structure and a three-dimensional arrangement of different classes of immunoglobulins are well known.

The antibody that may be purified using the HIC method provided in the present specification may be a monoclone or a polyclone. The "monoclonal antibody" refers to a homogeneous antibody population, and the "polyclonal antibody" refers to a heterogeneous antibody population.

In the exemplary embodiment of the disclosure, the antibody is a humanized antibody. The humanized antibody may refer to a specific chimera immunoglobulin, a non-human antibody having an immunoglobulin chain, or a form of the antigen-binding fragment of the antibody including a minimal sequence derived from human immunoglobulin. The humanized antibody may be a human immunoglobulin (recipient antibody) obtained in a manner that a residue from a complementarity determining region (CDR) of a recipient is replaced with a residue from the CDR of a non-human species (donor antibody) such as a mouse, a rat, a rabbit, or the like with desired specificity, affinity, and ability.

Examples of the antibody that may be purified using the chromatography carrier provided in the present specification include the following antibodies, but are not limited these antibodies. There are abagovomab, abciximab, actoxumab, adalimumab, adecatumumab, afelimomab, afutuzumab, alacizumab pegol, ALD, alemtuzumab, alirocumab, altumomab pentetate, amatuximab, anatumomab mafenatox, anrukinzumab, apolizumab, arcitumomab, aselizumab, atinumab, atlizumab, atorolimumab, bapineuzumab, basiliximab, bavituximab, bectumomab, belimumab, benralizumab, bertilimumab, besilesomab, bevacizumab, bezlotoxumab, biciromab, bimagrumab, bivatuzumab mertansine, blinatumomab, blosozumab, brentuximab vedotin, briakinumab, brodalumab, canakinumab, cantuzumab mertansine, cantuzumab ravtansine, caplacizumab, capromab pendetide, carlumab, catumaxomab, cedelizumab, certolizumab pegol, cetuximab, citatuzumab bogatox, cixutumumab, clazakizumab, clenoliximab, clivatuzumab tetraxetan, conatumumab, concizumab, crenezumab, dacetuzumab, daclizumab, dalotuzumab, daratumumab, demcizumab, denosumab, detumomab, dorlimomab aritox, drozitumab, duligotumab, dupilumab, dusigitumab, ecromeximab, eculizumab, edobacomab, edrecolomab, efalizumab, efungumab, eldelumab, elotuzumab, elsilimomab, enavatuzumab, enlimomab pegol, enokizumab, enoticumab, ensituximab, epitumomab cituxetan, epratuzumab, erlizumab, ertumaxomab, etaracizumab, etrolizumab, evolocumab, exbivirumab, fanolesomab, faralimomab, farletuzumab, fasinumab, FBTA, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, guselkumab, emicizumab, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lampalizumab, lebrikizumab, lemalesomab, lerdelimumab, lexatumumab, libivirumab, ligelizumab, lintuzumab, lirilumab, lodelcizumab, lorvotuzumab mertansine, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-CD, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pinatuzumab vedotin, pintumomab, placulumab, polatuzumab vedotin, ponezumab, priliximab, pritoxaximab, pritumumab, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, seribantumab, setoxaximab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, teneliximab, teplizumab, teprotumumab, TGN, ticilimumab, tildrakizumab, tigatuzumab, tocilizumab, toralizumab, tositumomab, tovetumab, tralokinumab, trastuzumab, TRBS, tregalizumab, tremelimumab, tucotuzumab celmoleukin, tuvirumab, ublituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, and zolimomab aritox.

In the exemplary embodiment of the disclosure, the absorbance meter is used to measure the concentration of the antibody solution.

In the exemplary embodiment of the disclosure, the antibody solution is loaded on the chromatography column, and next the loaded protein is extruded by the addition of a mobile phase buffer solution. In the embodiment, the protein may first be equilibrated in the mobile phase buffer solution before being loaded on the column. The purified protein may be collected, for example, as a flow-through fraction.

In the exemplary embodiment of the disclosure, a flow-through mode HIC is used. The flow-through mode HIC is frequently used to remove the dimer. The dimer has a chemical property quite similar to the monomer, but is generally more hydrophobic than the monomer. Under the conditions provided in the present specification, the dimer binds to the chromatography carrier of the column, allowing the monomer to flow through. Thereby, when used in the present specification, the flow-through refers to a protein in a mobile phase buffer agent collected in a fraction that has passed through a carrier-containing column provided in the present specification.

In the exemplary embodiment of the disclosure, a size exclusion chromatography is used to measure the amount of the dimer contained in the flow-through. Biomolecules can be separated based on molecular sizes in the solution by using the size exclusion chromatography.

EXAMPLE

Hereinafter, the disclosure is described in detail with reference to examples, but the content of the disclosure is not limited thereto.

Example 1

[Manufacture of 6% Spherical Cellulose Particle (Containing Water)]

A 6% spherical cellulose particle was manufactured according to the following procedure. Here, the cellulose particle manufactured when a concentration of a crystalline cellulose is 6% by weight in the following step (1) is referred to as the "6% spherical cellulose particle".

(1) 6.4 g of crystalline cellulose (manufactured by Asahi Kasei Corporation, trade name: Ceolus PH101) was added to 100 g of an aqueous solution containing 60% by weight of calcium thiocyanate, and the mixture was heated to 110 to 120° C., to be dissolved.

(2) 6 g of sorbitan monooleate was added to the solution as a surfactant. The solution was added dropwise to 480 mL of o-dichlorobenzene preheated to 130 to 140° C., and the mixture was stirred at 200 to 300 rpm to obtain a dispersion liquid.

(3) Next, the dispersion liquid was cooled to 40° C. The cooled dispersion liquid was poured into 190 mL of methanol to obtain a suspension of particles.

(4) The obtained suspension was filtered and separated to collect particles, and the particles were washed with 190 mL of methanol. The washing operation was performed several times.

(5) The particles were further washed with a large amount of water to obtain the 6% spherical cellulose particle.

(6) Next, the spherical cellulose particle was sieved according to JIS standard sieving spec of 53 to 125 μm to obtain the 6% spherical cellulose particle (containing water, cellulose dissolution concentration: 6% by weight) having a desired particle diameter (particle diameter; 50 to 150 μm, average particle diameter: about 100 μm).

Moreover, the average particle diameter here was measured using an image taken by the optical microscope. Specifically, the vernier caliper was used to measure a particle diameter on the image, and an original particle diameter was obtained from the photographing magnification. Then, the average particle diameter was calculated from values of each particle diameter obtained from the optical microscope image by the following formula.

$$\text{Volume average particle diameter (MV)}=\Sigma(nd^4)/\Sigma(nd^3)$$

[In the formula, d represents the value of the particle diameter of each particle obtained from the optical microscope image, and n represents the number of measured particles.]

[Manufacture of Crosslinked 6% Cellulose Particle]

The 6% spherical cellulose particle manufactured above was subjected to the crosslinking reaction to manufacture a crosslinked 6% cellulose particle. The procedure is as follows.

(1) 121 g of pure water was added to 100 g of the 6% spherical cellulose particle (containing water) obtained above, and the mixture was stirred and heated. When the temperature reached 30° C. 3.3 g of NaOH aqueous solution that is 45% by weight and 0.5 g of $NaBH_4$ were added, and the mixture was further heated and stirred. An initial alkali concentration here was 0.69% (w/w).

(2) After 30 minutes. 60 g of $Na_2SO_4$ was added to a reaction solution heated to 45° C. and dissolved. From a time point when the temperature of the mixture reached 50° C., the temperature was maintained at 50° C., and the stirring was further continued for 2 hours.

(3) The stirring of the mixture was continued at 50° C., and 48 g of NaOH aqueous solution that is 45% by weight and 50 g of epichlorohydrin, each divided into 25 equal parts, were added every 15 minutes for about 6 hours.

(4) After completion of the addition, the mixture was reacted at the temperature of 50° C., for 16 hours.

(5) After the reaction mixture was cooled to 40° C. 2.6 g of acetic acid was added to neutralize.

(6) The reaction mixture was filtered to recover the cellulose particle, and the cellulose particle was filtered and washed with the pure water to obtain the crosslinked 6% cellulose particle. An average particle diameter and a Kav value of the obtained crosslinked 6% cellulose particle were measured as follows.

(Measurement of Average Particle Diameter)

The average particle diameter was measured using the laser diffraction/scattering type particle diameter distribution measuring device LA-950 (a decrease rate of the dimer by purification of the HIC), and was 85 μm.

(Measurement of Kav Value)

The gel partition coefficient Kav was calculated by the following formula from the relationship between the retention capacitance and the column volume by using the standard polyethylene oxide having a weight average molecular weight of $1.5\times10^5$ Da as a sample. Moreover, the pure water was used as the mobile phase.

$$Kav=(Ve-V0)/(Vt-V0)$$

[In the formula, Ve represents a retention capacitance (mL) of the sample, Vt represents an empty column volume (mL), and V0 represents a retention capacitance (mL) of blue dextran.] A gel partition coefficient Kav of the crosslinked 6% cellulose particle obtained above was 0.37.

[Modification by Hydrophobicity]

15 g of the crosslinked 6% cellulose particles obtained above were placed in a 50 mL centrifuge tube, and 24 mL of pure water was added thereto to form a slurry. Thereafter, the temperature was raised to 28° C., and the slurry was stirred so that the gel flowed. 9.9 g of sodium sulfate was added, then 2.1 g of NaOH aqueous solution that is 48.6% by weight was added, and the mixture was stirred for 1 hour. 1.6 g of glycidyl phenyl ether (Tokyo Chemical Industry Co., Ltd.) was added, the temperature was adjusted to 50° C.±2° C., and the mixture was stirred and reacted for 16 hours. Thereafter, the mixture was washed 5 times with 100 mL of pure water at 50° C., 15 times with 100 mL of methanol, and 5 times with 100 mL of pure water to obtain cellulose particles modified with hydrophobic groups.

[Gradient Elution Test]

TOYOPEARL® Hexyl 650C (Tosoh Corporation), which is described in Patent literature 1 as a chromatography carrier having the highest hydrophobicity, is a HIC carrier obtained by introducing hexyl groups using a hydrophilic vinyl polymer as a base material and is obtained by introducing the hexyl groups into HW-65 (protein exclusion limit molecular weight 5×106) having a base material of the hydrophilic vinyl polymer. TOYOPEARL® Hexyl 650C (Tosoh Corporation) and the chromatography carrier of the disclosure were respectively packed in the column having a column volume of 1.06 mL, the preparative chromatography device was used, the 20 mM of sodium phosphate buffer solution containing 1 M of ammonium sulfate at pH 7.0 was flowed at a flow rate of 0.25 column volume/min for 5 column volumes, thereafter a 1 mg/mL lysozyme solution dissolved in the 20 mM of sodium phosphate buffer solution containing 1 M of ammonium sulfate at pH 7.0 was flowed at a flow rate of 0.25 column volume/min for 1 column volume, thereafter the 20 mM of sodium phosphate buffer solution containing the 1 M of ammonium sulfate at pH 7.0 was flowed at a flow rate of 0.25 column volume/min for 2 column volumes, thereafter the 20 mM of sodium phosphate buffer solution at pH 7.0 was flowed at a flow rate of 0.25 column volume/min for 10 column volumes, and then solutions at the time of the appearance of an elution peak top of lysozyme measured at a transmitted light of 280 nm by the absorbance meter having a flow cell with a capacity of 2 μL or less were measured by the electric conductivity meter having a flow cell with a capacity of 50 μL or less and connected to the absorbance meter via a tube having a capacity of 20 μL or less, and the obtained electric conductivities were compared. The lysozyme used was made by Roche. FIG. 1 shows linear retention data for each of the tested chromatography carriers. As shown, the chromatography carrier of the disclosure was eluted with a lower electric conductivity than the TOYOPEARLR Hexyl 650C. The chromatography carrier of the disclosure was eluted with an electric conductivity of 34 mS/cm, and the TOYOPEARL® Hexyl 650C was eluted with an electric conductivity of 64 mS/cm.

[Preparation of Antibody Solution]

1 L of culture supernatant of CHO cells containing mAb was purified with Protein A carrier CELLUFINE™ SPA-HC (manufactured by JNC Corporation) to obtain 180 mL of a solution. Next, 1 M of acetic acid was added to the solution to adjust the pH to 3.4, and the solution was allowed to stand at 25° C., for 1 hour to inactivate virus. 1 M of Tris was added to the solution after virus inactivation to adjust the pH to 6.0. An antibody concentration of the above solution was 13 mg/mL, the above solution was diluted with a buffer solution at pH 6.0 containing 20 mM of Tris acetate+50 mM of NaCl to be 5.7 mg/mL, and the diluted solution was used as a load sample. An antibody concentration of the load sample was calculated by measuring an absorbance at a wavelength of 280 nm with the absorbance meter and dividing the measured absorbance by 1.4. The amount of antibody of the load sample was calculated by multiplying a volume of the load sample by the antibody concentration. An electric conductivity of the load sample was measured using ES-71 (manufactured by HORIBA, Ltd.) and 3552-10D (manufactured by HORIBA, Ltd.), and was 7.7 mS/cm.

[Purification by HIC]

As a contrast, the TOYOPEARL® Hexyl 650C (Tosoh Corporation) and the chromatography carrier of the disclosure were respectively packed in the column having a column volume of 1.06 mL, the preparative chromatography device was used, the buffer solution at pH 6.0 containing 20 mM of Tris acetate+50 mM of NaCl was flowed at a flow rate of 0.25 column volume/min for 5 column volumes, thereafter 18.6 mL of the load sample was flowed at a flow rate of 0.25 column volume/min, and the buffer solution at pH 6.0 containing 20 mM of Tris acetate+50 mM of NaCl was flowed at a flow rate of 0.25 column volume/min for 10 column volumes. 18.6 mL of the load sample from the start of flowing and 10 column volumes of the buffer solution at pH 6.0 containing 20 mM of Tris acetate+50 mM of NaCl after the load sample was flowed were recovered collectively to form a flow-through pool (FT pool). The recovery amount of the antibody was calculated by multiplying a volume of the FT pool by an antibody concentration of the recovered solution.

[Analysis of Dimer Content]

The load sample and the FT pool were analyzed by the size exclusion chromatography to measure the content by percentage of the dimer. TSKgel® SuperSW mAb HR (Tosoh Corporation) was used as the column, TSKgel® guardcolumn SuperSW mAb (Tosoh Corporation) was used as a guard column, and a buffer solution at pH 6.7 containing 200 mM of sodium phosphate+100 mM of sodium sulfate was used as the mobile phase. The purified solution was diluted with the mobile phase to an antibody concentration of 1 mg/mL, and the diluted solution was analyzed under conditions of an injection amount of 50 μL, a column temperature of 25° C., and a flow rate of 0.7 mL/min. A monomer has a peak with a retention time of 12.5 minutes, a dimer has a peak with a retention time of 10.5 minutes, and an aggregate has a peak with a retention time of 7.8 minutes to 9.8 minutes before the dimer peak. The total of peak areas of the monomer, the dimer, and the aggregate peak was taken as a total antibody amount, and each ratio was calculated from the peak areas of the monomer, the dimer, and the aggregate. The amount of the antibody was multiplied by each ratio to calculate the amount of the monomer, the amount of the dimer, and the amount of the aggregate. A recovery rate of the monomer was calculated by dividing the amount of the monomer of the FT pool by the amount of the monomer of the load sample. A reduction rate of the dimer was calculated by dividing the amount of the dimer of the load sample by the amount of the dimer of the FT pool.

Table 1 shows the dimer content and the recovery rate of each of the tested chromatography carriers. A reduction rate of the dimer as a contrast was 2.8, whereas that of the chromatography carrier of the disclosure was 6.7, which was twice or more the reduction rate of the dimer as a contrast (TOYOPEARL® Hexyl 650C). There has never been a chromatography carrier that maintains the recovery rate of the monomer 90% or more and shows this reduction rate of the dimer in the flow-through mode, which was a surprising result.

TABLE 1

Reduction rate of dimer in purification by HIC

| Loading [g/L-resin] | Carrier | Recovery rate of monomer [%] | Load sample | | | FT pool | | | Reduction rate of dimer [-] |
|---|---|---|---|---|---|---|---|---|---|
| | | | Amount of monomer [mg] | Amount of aggregate [mg] | Amount of dimer [mg] | Amount of monomer [mg] | Amount of aggregate [mg] | Amount of dimer [mg] | |
| 100 | Contrast | 99.5 | 97.9 | 0.617 | 1.59 | 97.5 | 0.00 | 0.565 | 2.8 |
| | Carrier of the disclosure | 95.4 | | | | 93.4 | 0.00 | 0.237 | 6.7 |

Example 2

[Preparation of Antibody Solution]

1 L of culture supernatant of CHO cells containing mAb was purified with Protein A carrier CELLUFINE™ SPA-HC (manufactured by JNC Corporation) to obtain 180 mL of a solution. Next, 1 M of acetic acid was added to the solution to adjust the pH to 3.4, and the solution was allowed to stand at 25° C., for 1 hour to inactivate virus. 1 M of Tris was added to the solution after virus inactivation to adjust the pH to 7.0. Thereafter, 1 M of NaCl solution was added to the solution at pH 7.0 to adjust the electric conductivity to 10 mS/cm. An antibody concentration of the above solution was 10 mg/mL. CELLUFINE™ MAX IB (manufactured by JNC Corporation) packed in a column volume of 1.06 mL was equilibrated with a solution at pH 7.0 containing 20 mM of Tris acetate+10 mS/cm NaCl. A solution having an antibody concentration of 10 mg/mL was loaded into the equilibrated solution by 200 g/L-resin, and thereafter 15.9 mL of the solution at pH 7.0 containing 20 mM of Tris acetate+10 mS/cm NaCl was loaded into the equilibrated solution. The flow-through of the loaded antibody solution and the flow-through of 15.9 mL of the loaded solution were recovered collectively to be used as a load sample. An antibody concentration of the load sample was 3.38 mg/mL, the pH of the load sample was 7.0, and an electric conductivity of the load sample was 10 mS/cm. The antibody concentration was calculated by measuring an absorbance at a wavelength of 280 nm by the absorbance meter and dividing the measured absorbance by 1.4. The amount of antibody of the load sample was calculated by multiplying a volume of the load sample by the antibody concentration. The electric conductivity of the load sample was measured using ES-71 (manufactured by HORIBA, Ltd.) and 3552-10D (manufactured by HORIBA, Ltd.).

[Purification by HIC]

The chromatography carrier of the disclosure of Example 1 was packed in the column having a column volume of 1.06 mL, the preparative chromatography device was used, the solution at pH 7.0 containing 20 mM of Tris acetate+10 mS/cm NaCl was flowed at a flow rate of 0.25 column volume/min for 5 column volumes, thereafter 43.9 mL of the load sample was flowed at a flow rate of 0.25 column volume/min, and the solution at pH 7.0 containing 20 mM of Tris acetate+10 mS/cm NaCl was flowed at a flow rate of 0.25 column volume/min for 15 column volumes. 43.9 mL of the load sample from the start of flowing and 15 column volumes of the solution at pH 7.0 containing 20 mM of Tris acetate+10 mS/cm NaCl after the load sample was flowed were recovered collectively to form the flow-through pool (FT pool). The recovery amount of the antibody was calculated by multiplying a volume of the FT pool by an antibody concentration of the recovered solution.

[Analysis of Dimer Content]

The load sample and the FT pool were analyzed by the size exclusion chromatography to measure the content by percentage of the dimer. TSKgel® SuperSW mAb HR (Tosoh Corporation) was used as the column, TSKgel® guardcolumn SuperSW mAb (Tosoh Corporation) was used as the guard column, and the buffer solution at pH 6.7 containing 200 mM of sodium phosphate+100 mM of sodium sulfate was used as the mobile phase. The purified solution was diluted with the mobile phase to an antibody concentration of 1 mg/mL, and the diluted solution was analyzed under conditions of an injection amount of 50 μL, a column temperature of 25° C., and a flow rate of 0.7 mL/min. A monomer has a peak with a retention time of 12.5 minutes, a dimer has a peak with a retention time of 10.5 minutes, and an aggregate has a peak with a retention time of 7.8 minutes to 9.8 minutes before the dimer peak. The total of peak areas of the monomer, the dimer, and the aggregate peak was taken as a total antibody amount, and each ratio was calculated from the peak areas of the monomer, the dimer, and the aggregate. The amount of the antibody was multiplied by each ratio to calculate the amount of the monomer, the amount of the dimer, and the amount of the aggregate. A recovery rate of the monomer was calculated by dividing the amount of the monomer of the FT pool by the amount of the monomer of the load sample. A reduction rate of the dimer was calculated by dividing the amount of the dimer of the load sample by the amount of the dimer of the FT pool.

The chromatography carrier of the disclosure had a reduction rate of the dimer of 6.6, and a case of the addition of 140 g/L-resin also showed a reduction rate of the dimer of 6.6 (Table 2).

TABLE 2

Reduction rate of dimer in purification by HIC under 140 g/L-resin loading

| | | | | Load sample | |
|---|---|---|---|---|---|
| Loading [g/L-resin] | Electric conductivity [mS/cm] | pH | Recovery rate of monomer [%] | Amount of monomer [mg] | Amount of aggregate [mg] |
| 140 | 10 | 7 | 96.0 | 147 | 0 |

| | Load sample | FT pool | | | |
|---|---|---|---|---|---|
| Loading [g/L-resin] | Amount of dimer [mg] | Amount of monomer [mg] | Amount of aggregate [mg] | Amount of dimer [mg] | Reduction rate of dimer [-] |
| 140 | 1.11 | 142 | 0.00 | 0.168 | 6.6 |

[Purification Combining HIC and Mixed-Mode]

A Mixed-mode chromatography carrier is a carrier that engages in a plurality of interactions such as an electrostatic interaction, a hydrophobic interaction, a hydrogen bonding interaction, and the like with a subject matter or a foreign matter. The Mixed-mode chromatography carrier is known to be capable of separating the subject matter and the foreign matter under a wide range of conditions, as compared with a carrier that interacts on a single principle. In the following examples, a Mixed-mode carrier excellent in reducing a host cell protein (HCP) and a leaked protein A which are foreign matters in antibody purification, and the HIC carrier excellent in reducing the dimer of the disclosure were combined to carry out the antibody purification.

Example 3

[Preparation of Antibody Solution]

1.6 L of culture supernatant of CHO cells containing mAb was purified with Protein A carrier CELLUFINE™ SPA-HC (manufactured by JNC Corporation) to obtain 67 mL of a solution. Next, 1 M of acetic acid was added to the solution to adjust the pH to 3.4, and the solution was allowed to stand at 25° C., for 1 hour to inactivate virus. 1 M of Tris was added to the solution after virus inactivation to adjust the pH to 5.0. Furthermore, ultrapure water, 1 M of Tris, and 5 M of NaCl were added to the solution to adjust the pH to 7.0, adjust the electric conductivity to 10 mS/cm, and finally the solution was filtered through a filter of 0.2 μm. An antibody concentration of the above solution was 10.5 mg/mL.

[Purification with Mixed-Mode Carrier Column and HIC Column Directly Linked]

Figure 2A:
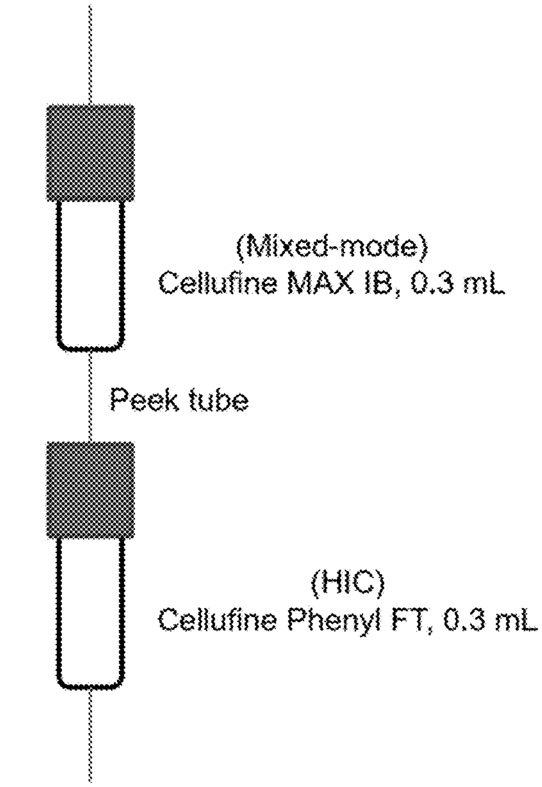
FIG. 2(*a*) and FIG. 2(*b*) are schematic diagrams of column arrangement in Examples 3 and 4.
Figure 2B:
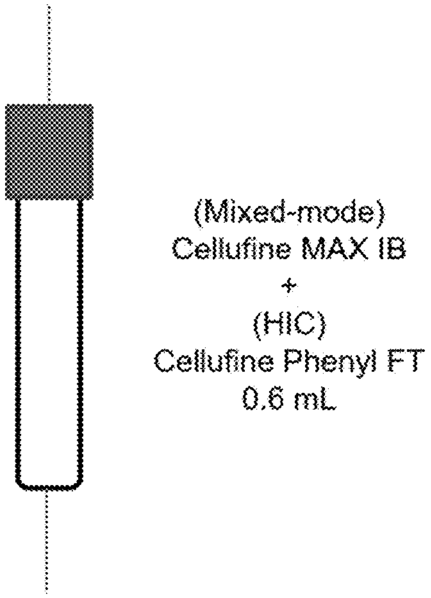

Mixed-mode carrier CELLUFINE™ MAX IB (manufactured by JNC Corporation) and HIC carrier CELLUFINE™ Phenyl FT (manufactured by JNC Corporation) manufactured by the same method as in Example 1 of the disclosure were respectively packed in a glass column having an inner diameter of 5 mm to a height of 1.5 cm. Next, the two columns were connected using a PEEK tube as shown in FIG. 2(*a*). The linked columns were connected to a preparative chromatography device, and the solution at pH 7.0 containing 20 mM of Tris acetate+10 mS/cm NaCl was passed through at a flow rate of 0.075 mL/min for equilibration. Next, 6.5 mL of the antibody solution was flowed at a flow rate of 0.075 mL/min, and thereafter 4.5 mL of the solution at pH 7.0 containing 20 mM of Tris acetate+10 mS/cm NaCl was flowed at a flow rate of 0.075 mL/min. Column passing liquids of 6.5 mL of the antibody solution and 4.5 mL of the solution at pH 7.0 containing 20 mM of Tris acetate+10 mS/cm NaCl thereafter were recovered collectively to form the flow-through pool (FT pool). The recovery amount of the antibody was calculated by multiplying a volume of the FT pool by an antibody concentration of the recovered solution.

Example 4

[Purification by Mixing and Packing Mixed-Mode Carrier and HIC Carrier in One Column]

Mixed-mode carrier CELLUFINE™ MAX IB (manufactured by JNC Corporation) and HIC carrier CELLUFINE™ Phenyl FT (manufactured by JNC Corporation) manufactured by the same method as in Example 1 of the disclosure were mixed at a volume conversion ratio of 1:1 to prepare a mixed slurry. The prepared slurry was added to the glass column having an inner diameter of 5 mm and packed to a height of 3 cm. (FIG. 2(*b*)) The packed column was connected to a preparative chromatography device, and the solution at pH 7.0 containing 20 mM of Tris acetate+10 mS/cm NaCl was passed through at a flow rate of 0.075 mL/min for equilibration. Next, 6.5 mL of the antibody solution prepared in the same manner as in Example 3 was flowed at a flow rate of 0.075 mL/min, and thereafter 4.5 mL of the solution at pH 7.0 containing 20 mM of Tris acetate+10 mS/cm NaCl was flowed at a flow rate of 0.075 mL/min. Column passing liquids of 6.5 mL of the antibody solution and 4.5 mL of the solution at pH 7.0 containing 20 mM of Tris acetate+10 mS/cm NaCl thereafter were recovered collectively to form the flow-through pool (FT pool). The recovery amount of the antibody was calculated by multiplying a volume of the FT pool by an antibody concentration of the recovered solution.

[Analysis of the Amount of HCP]

The amount of the HCP in the loaded antibody solution and the FT pool was measured using Elisa kit(*Cygnus*, F550). The obtained amount of the HCP and the amount of the antibody calculated from the absorbance at a measurement wavelength of 280 nm were used to show the amount of the HCP by a concentration (ppm) from a formula [the amount of HCP in FT pool (ng)/the amount of antibody in FT pool (mg)].

[Analysis of Leaked Protein A]

The amount of leaked protein A in the loaded antibody solution and the FT pool was measured using Elisa kit (*Cygnus*, F910). The obtained amount of leaked protein A and the amount of the antibody calculated from the absorbance at a measurement wavelength of 280 nm were used to show the amount of the HCP by a concentration (ppm) from a formula [the amount of leaked protein A in FT pool (ng)/the amount of antibody in FT pool (mg)].

Figure 3:
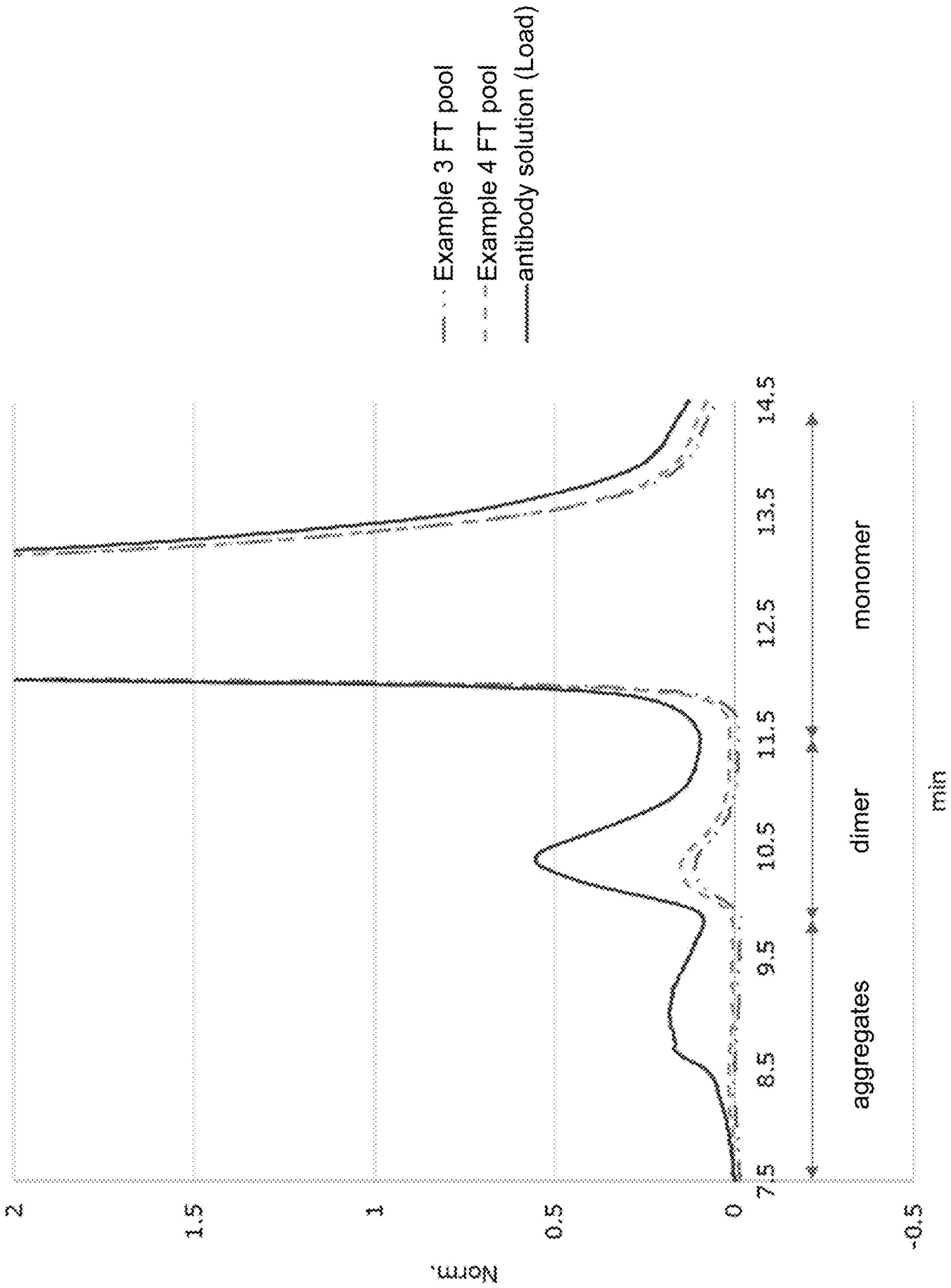
FIG. 3 is a chromatogram of size exclusion chromatographic analysis in Examples 3 and 4.

Analysis results of the FT pool obtained in Examples 3 and 4 were shown in Table 3, and a chromatogram of size exclusion chromatographic analysis was shown in FIG. 3.

When the HIC carrier of the disclosure was linked to or mixed with the Mixed-mode carrier, the foreign matter was highly reduced even though the antibody solution under the same condition was passed through different carriers. Because different chromatographic carriers usually have different suitable conditions respectively, the adjustment of solution conditions between the columns is necessary, but when the HIC carrier of the disclosure is used, the operation of the adjustment becomes unnecessary, and antibody purification can be performed more easily.

TABLE 3

Analysis results of antibody solution and FT pool after column purification

| Analysis sample | Recovery rate of monomer (%) | Size exclusion chromatographic analysis result (%) Monomer | Dimer | Aggregate | HCP (ppm) | Leaked protein A (ppm) |
|---|---|---|---|---|---|---|
| Antibody solution (Load) | — | 98.6 | 0.9 | 0.5 | 2200 | 2.6 |
| Example 3 FT pool | 89 | 99.8 | 0.2 | 0 | 26 | 0.1 |
| Example 4 FT pool | 89 | 99.8 | 0.2 | 0 | 29 | 0.1 |

INDUSTRIAL APPLICABILITY

According to the disclosure, a chromatography carrier suitable for removing a dimeric antibody, and a method for purifying a protein using the same can be provided.

What is claimed is:

1. A method for purifying an antibody of which a dimer is removed, the method comprising:

(1) selecting a chromatography carrier having a base carrier, wherein the base carrier comprises porous particles and a hydrophobic ligand bound to the base carrier, wherein the selecting comprises:

(a) performing a gradient elution test, comprising:

flowing a lysozyme solution comprising a buffer through the chromatography carrier and allowing the lysozyme solution to elute from the chromatography carrier, and measuring electric conductivity of the buffer of the lysozyme solution at the top of the elution peak of the lysozyme solution; and (b) selecting the chromatography carrier when the buffer of the lysozyme solution has an electric conductivity of 34 mS/cm or less at the top of the elution peak of the lysozyme solution; and (2) bringing the selected chromatography carrier into contact with an antibody solution comprising a dimer of an antibody; and (3) recovering a solution from the selected chromatography carrier, wherein the dimer has been removed from the recovered solution.

2. The method for purifying an antibody according to claim 1, wherein the step of contacting the chromatography carrier with the antibody solution comprises a step of passing the antibody solution through a container containing the chromatography carrier in a flow-through mode.

3. The method for purifying an antibody according to claim 1, wherein the antibody is a monoclonal antibody or a polyclonal antibody.

4. The method for purifying an antibody according to claim 3, wherein the antibody is a human antibody, a mouse antibody, or a chimeric antibody.

5. The method for purifying an antibody according to claim 1, wherein the lysozyme solution comprises a sodium phosphate buffer containing ammonium sulfate.

6. The method for purifying an antibody according to claim 5, wherein the flow rate of the lysozyme solution through the chromatography carrier is 0.25 column volume/min.

* * * * *